United States Patent
Ducke et al.

(10) Patent No.: US 8,579,959 B2
(45) Date of Patent: Nov. 12, 2013

(54) RADIOPAQUE REINFORCING MEMBER

(75) Inventors: Werner Dieter Ducke, Eight Mile Plains (AU); David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/062,593

(22) PCT Filed: Sep. 11, 2009

(86) PCT No.: PCT/US2009/005096
§ 371 (c)(1),
(2), (4) Date: Apr. 6, 2011

(87) PCT Pub. No.: WO2010/030370
PCT Pub. Date: Mar. 18, 2010

(65) Prior Publication Data
US 2011/0190868 A1    Aug. 4, 2011

Related U.S. Application Data

(60) Provisional application No. 61/191,882, filed on Sep. 12, 2008.

(51) Int. Cl.
*A61F 2/82* (2013.01)
(52) U.S. Cl.
USPC .......................................... 623/1.15
(58) Field of Classification Search
USPC ................................ 623/1.15–1.36
See application file for complete search history.

(56) References Cited

U.S. PATENT DOCUMENTS

| 4,041,931 | A  | * | 8/1977 | Elliott et al. ................. | 128/899 |
| 6,019,736 | A  | * | 2/2000 | Avellanet et al. ............. | 600/585 |
| 7,413,573 | B2 | * | 8/2008 | Hartley et al. ................ | 623/1.13 |
| 7,708,771 | B2 | * | 5/2010 | Chuter et al. ................. | 623/1.13 |
| 7,862,604 | B1 | * | 1/2011 | Marcade et al. ............... | 623/1.13 |
| 2002/0091439 | A1 | * | 7/2002 | Baker et al. ................... | 623/1.36 |
| 2003/0135971 | A1 | * | 7/2003 | Liberman et al. ............. | 29/419.1 |

(Continued)

FOREIGN PATENT DOCUMENTS

| WO | WO94/13268 | 6/1994 |
| WO | WO97/37616 | 10/1997 |

(Continued)

OTHER PUBLICATIONS

International Search Report and Written Opinion for PCT/US2009/005096 dated Nov. 25, 2009, 14 pgs.

*Primary Examiner* — Suzette J Gherbi
(74) *Attorney, Agent, or Firm* — Brinks Gilson & Lione

(57) ABSTRACT

A reinforcement member (10) for a fenestration in a stent graft (30) comprises a composite wire (12) formed from wire strands of at least two types (14, 16, 18). A first type of wire strand comprises a metal alloy with shape memory characteristics and a second type of wire strand comprising a metal with radiopaque characteristics. The first type of wire strand and the second type of wire strand are twisted or braided together to form the composite wire and then formed into the circular ring with at least two turns of the composite wire forming the ring. The reinforcement member can be a circular ring mounted into a fenestration (40) in a wall (32) of a stent graft, or mounted around a stent graft, or it can be a substantially U-shaped edging along the edge of a scalloped fenestration (44).

10 Claims, 2 Drawing Sheets

(56) References Cited

U.S. PATENT DOCUMENTS

2006/0004440 A1 1/2006 Stinson
2011/0295359 A1* 12/2011 Clerc et al. .................. 623/1.15
2012/0150277 A1* 6/2012 Wood et al. .................. 623/1.15

FOREIGN PATENT DOCUMENTS

| WO | WO2005/034808 | 4/2005 | |
| WO | WO 2005034808 A1 * | 4/2005 | ................ A61F 2/06 |
| WO | WO2007/095283 | 8/2007 | |

* cited by examiner

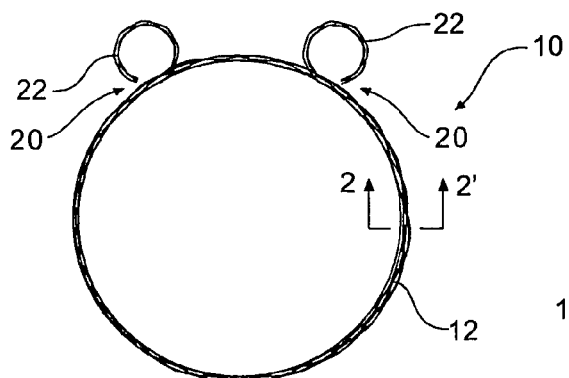
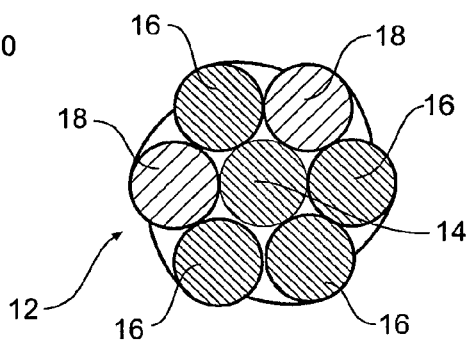
*Fig 1*
*Fig 2*
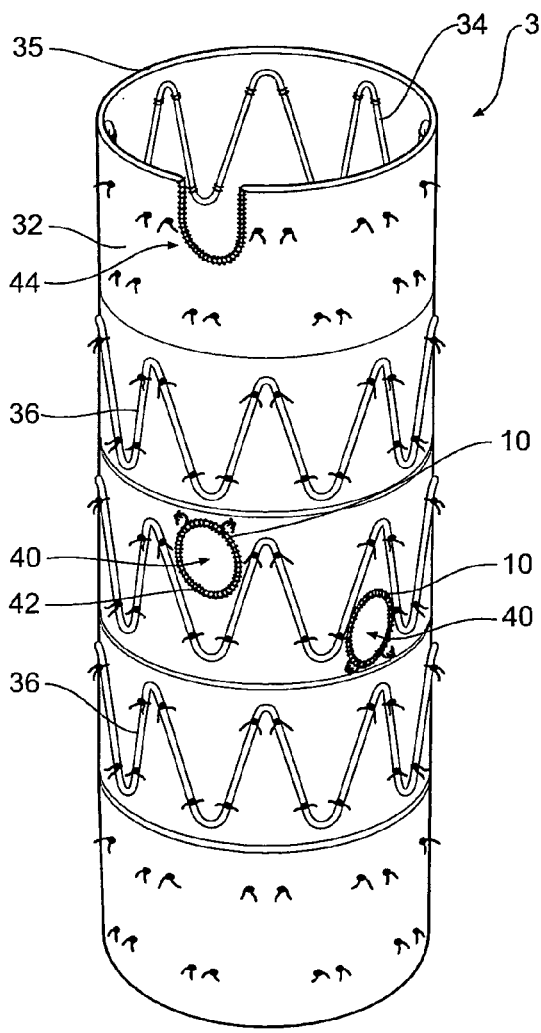
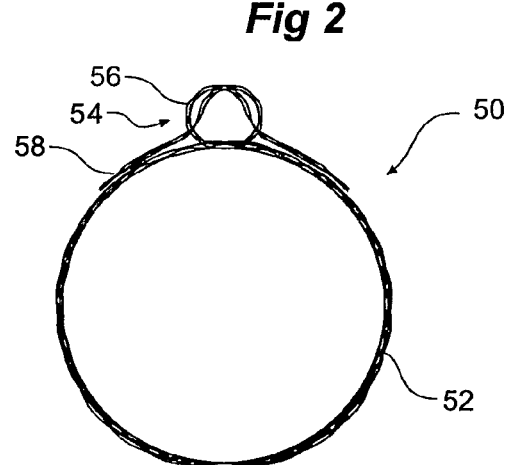
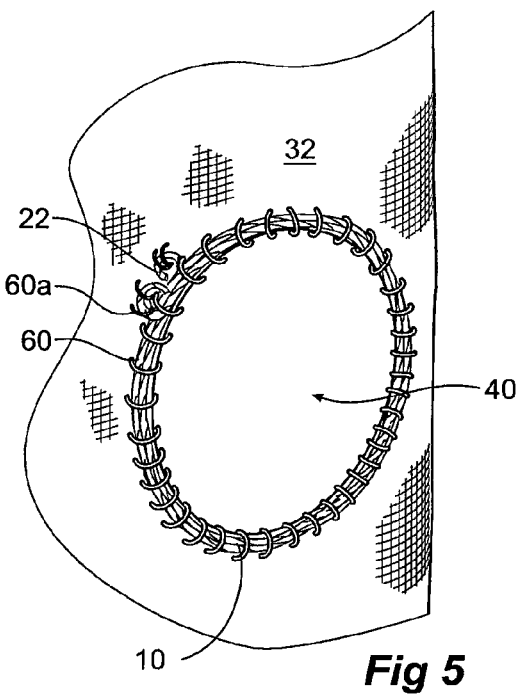
*Fig 3*
*Fig 4*
*Fig 5*

RADIOPAQUE REINFORCING MEMBER

RELATED APPLICATIONS

The present patent document is a §371 filing based on PCT Application Serial No. PCT/US2009/005096, filed Sep. 11, 2009 (and published as WO 2010/030370 A1 on Mar. 18, 2010), designating the United States and published in English, which claims the benefit of the filing date under 35 U.S.C. §119(e) of Provisional U.S. Patent Application Ser. No. 61/191,882, filed Sep. 12, 2008. All of the foregoing applications are hereby incorporated by reference in their entirety.

TECHNICAL FIELD

This invention relates to a medical device and more particularly to a reinforcing member used in a stent graft device.

BACKGROUND ART

Stent grafts are used to bridge a defect in the vasculature of a patient and can be deployed into the vasculature by endovascular techniques. This requires that the device can be constrained into a small delivery device and be able to expand or be expanded when release within the vasculature.

Where there is a side branch artery to the vasculature it may be necessary to provide an aperture in the stent graft, known as a fenestration, to enable access from a deployed stent graft to that side branch artery. Such a fenestration may be reinforced with a peripheral circular ring stitched to the graft material around the fenestration. It is also desirable in some situations to provide a side branch stent graft extending through the fenestration and into the side branch artery.

To obtain a good seal of the branch stent graft within the fenestration an inflatable balloon can be used to expand the branch stent graft into the fenestration and for this purpose the reinforcing ring must be able to resist expansion of its diameter. At the same time the ring must be resilient so that it can be distorted into its deployment configuration but when released expand back to its circular configuration. In this specification the term resilient when used in relation to a wire used to manufacture a reinforcing ring refers to a wire which is substantially inextensible but which has a spring function so that when distorted and released returns to its original configuration.

Generally such reinforcing rings are manufactured from a metal known as a shape memory metal such as, but not restricted to, a nickel titanium alloy known as Nitinol. To form a ring of a shape memory metal the desired final shape is formed from a wire on a former and then the wire on the former is heated above a temperature which sets the wire in the new shape. Upon cooling the ring holds its formed shape and can be distorted and resiliently returns to the formed shape.

It is also desirable that the position of reinforcing ring on a stent graft when the stent graft is deployed within the vasculature be able to be visualised. Nitinol, from which reinforcing rings have been constructed is not radiopaque and hence it has been necessary to use radiopaque markers adjacent the reinforcing ring to denote its position.

DISCLOSURE OF THE INVENTION

Aspects of the present invention seek to provide a reinforcing member which is radiopaque but still has the necessary resiliency and shape memory characteristics.

This invention will be discussed in relation to the application of reinforcing member to fenestrations but such members have alternative applications in other situations and the invention extends to those other uses as well, for example to a scalloped fenestration at the end of a stent graft. Alternatively, they can be applied around the entire periphery of a stent graft, particularly around the end thereof.

According to a first aspect of the present invention, there is provided a reinforcement member for a fenestration in a stent graft, the reinforcement member comprising a composite wire, having wire strands of at least two types, a first type of wire strand comprising a metal alloy with shape memory characteristics and a second type of wire strand comprising a metal with radiopaque characteristics, the first type of wire strand and the second type of wire strand being twisted or braided together to form the composite wire and then formed into the reinforcement member with at least a double strand of the composite wire throughout the extent of the reinforcement member.

According to a second aspect of the present invention, there is provided a stent graft member comprising a reinforcing member according to the first aspect.

Preferably, the reinforcement member is in the form of a ring comprising from 3 to 6 wire strands of the first type of strand and from 2 to 4 wire strands of the second type of strand.

The first type of wire strand is a nickel titanium alloy to give the shape memory characteristics and the second type of wire strand comprises a metal selected from gold, silver and platinum to give the radiopaque characteristics.

In a preferred embodiment there are seven strands in the composite wire, the seven wire strands comprising one nickel titanium alloy core wire strand, four nickel titanium alloy peripheral wire strands and two platinum peripheral wire strands.

In a preferred embodiment the composite wire has a diameter of 0.009 in. (0.23 mm), the nickel titanium alloy wire strands have a diameter of 0.003 in. (0.076 mm) and the platinum wire strands have a diameter of 0.003 in. (0.076 mm).

One preferred embodiment of the invention comprises a circular ring reinforcement for a fenestration in a stent graft, the ring reinforcement comprising a planar circular ring of a composite wire, the composite wire comprising a plurality of wire strands of at least two types, a first type of wire strand comprising a metal alloy with shape memory characteristics and a second type of wire strand comprising a metal with radiopaque characteristics, the first type of wire strand and the second type of wire strand being twisted or braided together to form the composite wire and then formed into the circular ring with about at least two turns of the composite wire forming the ring.

In a preferred embodiment the ring comprises terminal ends at each end of the wire, the terminal ends each comprising a loop of the composite wire. Preferably the terminal loops of the wire at each end of the wire overlap. Alternatively there are two complete circular turns of the wire and the loops are further around the circular ring.

In an alternative embodiment the composite ring comprises terminal ends at each end of the wire, the terminal ends each comprising a loop and a tail, the tail being folded back and extending around the circular ring.

The use of reinforcing rings of the type described herein is disclosed and discussed in PCT Publication WO/2005034808 entitled "FENESTRATED STENT GRAFTS" and the disclosed thereof is incorporated herein in its entirety.

BRIEF DESCRIPTION OF THE DRAWINGS

Preferred embodiments of the present invention will now be described, by way of example only, with reference to the accompanying drawings, of which:

FIG. 1 shows a first embodiment of an opaque reinforcing ring according to the present invention;

FIG. 2 shows a detail cross section along the line 2-2' of the opaque reinforcing ring shown in FIG. 1;

FIG. 3 shows a stent graft incorporating reinforcing rings of the type shown in FIG. 1;

FIG. 4 shows an alternative embodiment of an opaque reinforcing ring according to the present invention; and FIG. 5 shows detail of a fenestration in a stent graft reinforced by a radiopaque reinforcing ring according to the present invention.

BEST MODE FOR CARRYING OUT THE INVENTION

Figure 6:
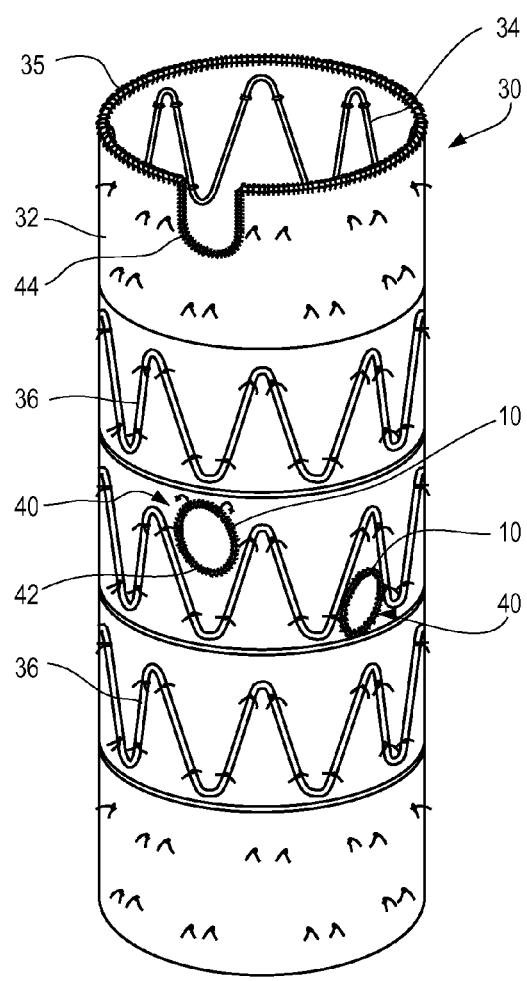
FIG. 6 shows reinforcing rings around the edge of the stent graft and around a scalloped fenestration.

Referring to the drawings, an embodiment in the form of the circular ring reinforcement is shown in FIGS. 1 and 2, and the circular ring reinforcement in use is shown in FIG. 3. It will be see that the opaque reinforcing ring 10 according to the present invention comprises a plurality of turns of a composite twisted or braided wire 12. Preferably there are about two turns of the wire although other numbers of turns may be used. As can be seen particularly in the cross sectional view of the wire in FIG. 2, the wire 12 comprises a core 14 of a nickel titanium alloy, four peripheral strands 16 of a nickel titanium alloy and two strands 18 of a radiopaque wire such as gold, silver or platinum. The gold, silver or platinum wire provides a radiopaque characteristic to the composite wire and the nickel titanium alloy gives shape memory characteristics to the composite wire.

The wire 12 can alternatively comprise, in an alternative embodiment, a core 14 of a nickel titanium alloy, two or three peripheral strands 16 of a nickel titanium alloy and three or four strands 18 of a radiopaque wire such as gold, silver and platinum. The total number of wires in the composite wire can also vary.

The wire 12 is formed into a planar circular shape and the terminal ends 20 of the wire 12 are formed into loops 22. In this embodiment the loops form a small circle. The loops 22 are provided to prevent the chance of damage to a lumen wall because the pointed ends of the composite wire are effectively enclosed within the respective loops.

FIG. 3 shows reinforcing rings according to the present invention used as a reinforcement for a fenestration of a stent graft. The stent graft 30 comprises a tubular wall 32. The tubular wall can be a biocompatible graft material such as Dacron, Thoralon™ (a polyurethane material), expanded PTFE material or a naturally occurring biomaterial, such as an extracellular matrix, such as small intestinal submucosa or other suitable material. Gianturco style zig zag Z stents 34 are provided inside the graft material of the tubular wall 32 at each end and between the ends Gianturco style zig zag Z stents 36 are provided on the outside of the graft material. There may be further Gianturco style zig zag Z stents on the tubular wall than those illustrated depending upon the overall length of the stent graft 30.

In the tubular wall 32 there is at least one substantially circular fenestration or aperture 40 on the tubular wall of the stent graft. In this embodiment there are two fenestrations 40 being one for each of the two renal arteries when this embodiment is deployed into the aorta. Other numbers of fenestrations may also be used where the placement of the stent graft involves the possibility of occluding other branch vessels such as the superior mesenteric artery. The fenestrations 40 are substantially circular.

A ring 10 of the type shown in FIGS. 1 and 2 is provided around the periphery of each fenestration 40 to give good dimensional stability to the fenestration 40. Stitching 42 is provided to retain the ring 10 around the periphery of the fenestration 40.

Also in FIG. 3 there is shown a scalloped fenestration 44 which opens to the end 35 of the stent graft. The scalloped fenestration 44 may also be reinforced with a radiopaque shape memory wire of the present invention. This reinforcing member is substantially U-shaped. The composite wire forming the reinforcement member may be doubled back on itself to provide a reinforcement member with two strands of composite wire.

FIG. 4 shows an alternative embodiment of reinforcing ring according to the present invention. In this embodiment the opaque reinforcing ring 50 according to the present invention comprises a plurality of turns of a composite twisted wire 52. Preferably there are about two turns of the wire although other numbers of turns may be used. The composite twisted wire 52 comprises a core of a nickel titanium alloy, three peripheral strands of a nickel titanium alloy and three strands of a radiopaque wire such as gold, silver and platinum. The gold, silver and platinum wire provides a radiopaque characteristic to the composite wire and the nickel titanium alloy gives shape memory characteristics to the composite wire.

The wire 52 is formed into a planar circular shape and the terminal ends 54 of the wire 52 are formed into loops 56. In this embodiment the loops 56 form a small circle and then a tail 58. The loop 56 is generally of a diameter through which can be passed a needle during stitching of the reinforcing ring into a graft material. Typically the loops may have a diameter of from 1 mm to 2 mm. The tail 58 extends back around the periphery of the reinforcing ring. The loops 56 and tail 58 are provided to prevent the chance of damage to lumen wall in use. When stitched into a stent graft the tails are held in by the stitching which holds the ring at the periphery of a fenestration. In this embodiment the loops 56 overlap each other. When stitched around a fenestration with at least one stitch passing through both loops the ring withstand expansion forces within it during placement of a balloon expandable stent through it. The stitched loops help to resist circumferential or diametral expansion.

The rings 10 and 50 can have a diameter of from 4 to 15 mm when they are used as a reinforcing ring for a fenestration and from 10 to 40 mm when they are used as an end reinforcement for a tubular stent graft. In one embodiment the composite wire has a diameter of 0.009 in. (0.23 mm), the nickel titanium alloy strands have a diameter of 0.003 in. (0.076 mm) and the platinum strands have a diameter of 0.003 in. (0.076 mm).

FIG. 5 shows a detail of a reinforcing ring of the type shown in FIG. 1 stitched around a fenestration 40. The ring 10 is stitched by stitching 60 around a fenestration 40 in a graft material 32. The loops 22 lie flat onto the graft material and are stitched by stitches 60a to the graft material.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A reinforcement member for a fenestration in a stent graft, the reinforcement member comprising a composite wire, having wire strands of at least two types, a first type of wire strand comprising a metal alloy with shape memory characteristics and a second type of wire strand comprising a metal with radiopaque characteristics, the first type of wire strand and the second type of wire strand being twisted or braided together to form the composite wire and then formed into the reinforcement member with at least a double strand of the composite wire throughout the extent of the reinforcement member, the reinforcement member comprising a substantially planar circular ring having at least two turns of the composite wire, where the ring comprises terminal ends at each end of the wire, the terminal ends each comprising a loop and a tail of the composite wire, the tail being folded back and extending around at least a portion of the circular ring, and wherein the terminal loops at each end of the wire overlap.

2. The reinforcement member of claim 1 where the composite wire comprises from 3 to 6 wire strands of the first type of wire strand and from 2 to 4 wire strands of the second type of wire strand.

3. The reinforcement member of claim 1 where the first type of wire strand is a nickel titanium alloy to give the shape memory characteristics and the second type of wire strand comprises a metal selected from gold, silver and platinum to give the radiopaque characteristics.

4. The reinforcement member of claim 1 where there are seven wire strands in the composite wire, the seven strands comprising one nickel titanium alloy core strand, four nickel titanium alloy peripheral strands and two platinum peripheral strands.

5. The reinforcement member of claim 4 where the composite wire has a diameter of about 0.009 in., the nickel titanium alloy wire strands have a diameter of about 0.003 in. and the platinum wire strands have a diameter of about 0.003 in.

6. A stent graft comprising:

a reinforcement member for at least one fenestration in the stent graft, the reinforcement member comprising a composite wire having wire strands of at least two types, a first type of wire strand comprising a metal alloy with shape memory characteristics and a second type of wire strand comprising a metal with radiopaque characteristics, the first type of wire strand and the second type of wire strand being twisted or braided together to form the composite wire and then formed into the reinforcement member with at least a double strand of the composite wire throughout the extent of the reinforcement member the reinforcement member comprising a substantially planar circular ring, where the ring comprises terminal ends at each end of the wire, the terminal ends each comprising a loop and a tail of the composite wire, the tail being folded back and extending around at least a portion of the circular ring.

7. The stent graft of claim 6 where at least one fenestration is disposed through the graft material at a location spaced from the ends of the graft member, where the reinforcement member is in the form of a ring around the edge of the at least one fenestration.

8. The stent graft of claim 6 further having a scalloped fenestration at an end thereof, the reinforcement member being located along the edge of the scalloped fenestration.

9. The stent graft of claim 6 where the reinforcement member extends around the periphery of the stent graft.

10. The stent graft of claim 9 where the reinforcement member is in the form of a ring around the edge of an end of the stent graft.

* * * * *